US011798680B2

United States Patent
MacDonald et al.

(10) Patent No.: US 11,798,680 B2
(45) Date of Patent: Oct. 24, 2023

(54) NURSE CALL SYSTEM WITH WIRELESS SOFTWARE UPDATING

(71) Applicant: Curbell Medical Products, Inc., Orchard Park, NY (US)

(72) Inventors: Daniel J. MacDonald, East Amherst, NY (US); Thomas Wilbur Rutherford, Buffalo, NY (US); Thomas P. Kennedy, Lake View, NY (US); Benjamin Rood, Amherst, NY (US)

(73) Assignee: Curbell Medical Products, Inc., Orchard Park, NY (US)

( * ) Notice: Subject to any disclaimer, the term of this patent is extended or adjusted under 35 U.S.C. 154(b) by 330 days.

(21) Appl. No.: 16/430,683

(22) Filed: Jun. 4, 2019

(65) Prior Publication Data

US 2020/0388377 A1    Dec. 10, 2020

(51) Int. Cl.
*G16H 40/20* (2018.01)
*G16H 40/67* (2018.01)
*G06F 8/65* (2018.01)

(52) U.S. Cl.
CPC ............ *G16H 40/20* (2018.01); *G06F 8/65* (2013.01); *G16H 40/67* (2018.01)

(58) Field of Classification Search
CPC .... G08B 5/222; G08B 25/009; G08B 25/016; G08B 21/0446; G08B 21/0461; G08B 21/22; G08B 25/00; G08B 7/06; G08B 25/014; G08B 25/08; G16H 40/20; G16H 40/67; G16H 40/63; G16H 40/40; G06F 8/65; G06F 8/654
See application file for complete search history.

(56) References Cited

U.S. PATENT DOCUMENTS

| | | | |
|---|---|---|---|
| 8,536,990 B2 * | 9/2013 | Collins, Jr. ............ | A61B 5/742 340/286.07 |
| 2009/0217080 A1 * | 8/2009 | Ferguson ................ | G08B 25/00 714/4.1 |
| 2014/0109075 A1 * | 4/2014 | Hoffman ............. | G06F 11/1464 717/169 |

* cited by examiner

*Primary Examiner* — Maroun P Kanaan
(74) *Attorney, Agent, or Firm* — Hodgson Russ LLP

(57) ABSTRACT

The present disclosure may be embodied as a nurse call system. The nurse call system may include a patient hub. The patient hub may include a nurse call interface circuit configured to be in electronic communication with a nurse call patient station. The patient hub may further include a hub controller in electronic communication with the nurse call interface circuit. The nurse call system may further include a patient interaction device ("PID"). The PID may include a hub interconnect configured to be in electronic communication with the hub controller. The PID may further include a wireless communication link for receiving a PID software update. The PID software update may be a PID firmware update. The PID software update may be a PID operating system update.

30 Claims, 3 Drawing Sheets

NURSE CALL SYSTEM WITH WIRELESS SOFTWARE UPDATING

FIELD OF THE DISCLOSURE

The present disclosure is generally directed to nurse call systems for use in hospital environments, and more particularly, to the wireless updating of electronic components of such nurse call systems.

BACKGROUND OF THE DISCLOSURE

Healthcare facilities, such as hospitals, are diverse settings offering many different types of care across many different wards. Care offered at a facility may encompass general or acute, intensive, specialized, rehabilitative, long-term, pediatric, geriatric, psychiatric, and other varieties of care. Different campuses, buildings within a campus, or wards within a building may be dedicated to providing each type of care to their corresponding patients.

Nurse call functionality is often an integral component of the diverse care settings and services offered. Whether the same nurse call system is installed across an entire campus or building, or localized to a particular ward or even newly-installed hospital wing, the healthcare services provided alongside nurse call are often fractured across wards. For example, a ward dedicated to childbirth care may provide one set of services that differ from services provided in a ward dedicated to long-term care and rehabilitation. Room environmental controls are another type of service that may vary across wards or even rooms, as some rooms may offer "scenes," for example, that set different lighting styles as a form of complementary therapy.

Furthermore, patient engagement and education have increasingly become important services provided as part of an overall care experience. Material may be offered to inform the patient about the condition they are being treated for and what to expect during the recovery process. Vital health data being monitored by the caregivers may be offered to the patient so they understand and are engaged with the treatment process. Many other innovative services exist, and new services continue to be developed and deployed to offer patients richer, more comprehensive services.

Traditionally, pillow speaker systems providing nurse call and basic entertainment functions to the patient are deployed using common hardware and fixed, static software. Different component part numbers (SKUs) may exist to offer different types of nurse call notifications, room environmental controls, entertainment functions, and compatibility with entertainment systems. Nevertheless, once deployed throughout a hospital setting, the pillow speaker and corresponding offered services remain static unless the unit is swapped out or reconfigured through direct, physical intervention.

As pillow speaker systems evolve into more comprehensive platforms offering a variety of modern capabilities, such as improved audio, high-quality video display, internet connectivity, access to mobile applications ("apps"), and custom apps tailored to complement the care services, using a static software image is increasingly undesirable.

Accordingly, there is a critical need for pillow speaker systems capable of updating their software without direct, physical intervention.

BRIEF SUMMARY OF THE DISCLOSURE

In an aspect of the present disclosure, a nurse call system is presented. The nurse call system may include a patient hub. The patient hub may include a nurse call interface circuit configured to be in electronic communication with a nurse call patient station. The patient hub may further include a hub controller in electronic communication with the nurse call interface circuit. The nurse call system may further include a patient interaction device ("PID"). The PID may be a pillow speaker. The PID may include a hub interconnect configured to be in electronic communication with the hub controller. The PID may further include a wireless communication link for receiving a PID software update. The PID software update may be a PID firmware update. The PID software update may be a PID operating system update.

The PID may further include a PID memory unit. The PID may be configured to load the PID software update into the PID memory unit. In one embodiment, the PID may be configured to load the PID software update into the PID memory unit only if the PID software update has been verified as genuine. The PID may further include a PID memory recovery module configured to load a previous PID software version into the PID memory unit if the PID software update fails to load.

The PID may be configured to produce a confirmation sound when the PID software update is successfully programmed into the PID memory unit. The confirmation sound may be produced by an audio speaker.

The PID may be configured to produce a confirmation notice when the PID software update is successfully programmed into the PID memory unit. The confirmation notice may be shown by a display screen.

The PID may be further configured to receive a hub software update received via the wireless communication link. The PID may be further configured to transmit the hub software update to the hub controller via the hub interconnect. The PID may be a pillow speaker. The hub software update may be a hub firmware update.

The hub controller may include a hub memory unit. The hub controller may be configured to load the hub software update into the hub memory unit. In one embodiment, the hub controller may be configured to load the hub software update into the hub memory unit only if the hub software update has been verified as genuine. The hub controller may further include a hub memory recovery module configured to load a previous hub software version into the hub memory unit if the hub software update fails to load.

The PID may be configured to produce a confirmation sound when the hub software update is successfully programmed into the hub memory unit. The confirmation sound may be produced by an audio speaker.

The PID may be configured to display a confirmation notice when the hub software update is successfully programmed into the hub memory unit. The confirmation notice is shown by a display screen.

The PID may be further configured to receive a nurse call software update received via the wireless communication link. The PID may be further configured to transmit the nurse call software update to the hub controller via the hub interconnect. The hub controller may be configured to transmit the nurse call software update to the nurse call interface circuit via an intrahub communication link. The nurse call software update may be a nurse call firmware update. The PID may be a pillow speaker.

The nurse call interface circuit may include a nurse call memory unit. The nurse call interface circuit may be configured to load the nurse call software update into the nurse call memory unit. In one embodiment, the nurse call interface circuit may be configured to load the nurse call software update into the nurse call memory unit only if the nurse call software update has been verified as genuine. The nurse call interface circuit may further include a nurse call memory recovery module configured to load a previous nurse call software version into the nurse call memory unit if the nurse call software update fails to load.

The PID may be configured to produce a confirmation sound when the nurse call software update is successfully programmed into the nurse call memory unit. The confirmation sound may be produced by an audio speaker.

The PID may be configured to display a confirmation notice when the nurse call software updated is successfully programmed into the nurse call memory unit. The confirmation notice may be shown by a display screen.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
FIG. 1 is an embodiment of a patient interface devices ("PID")
Figure 2:
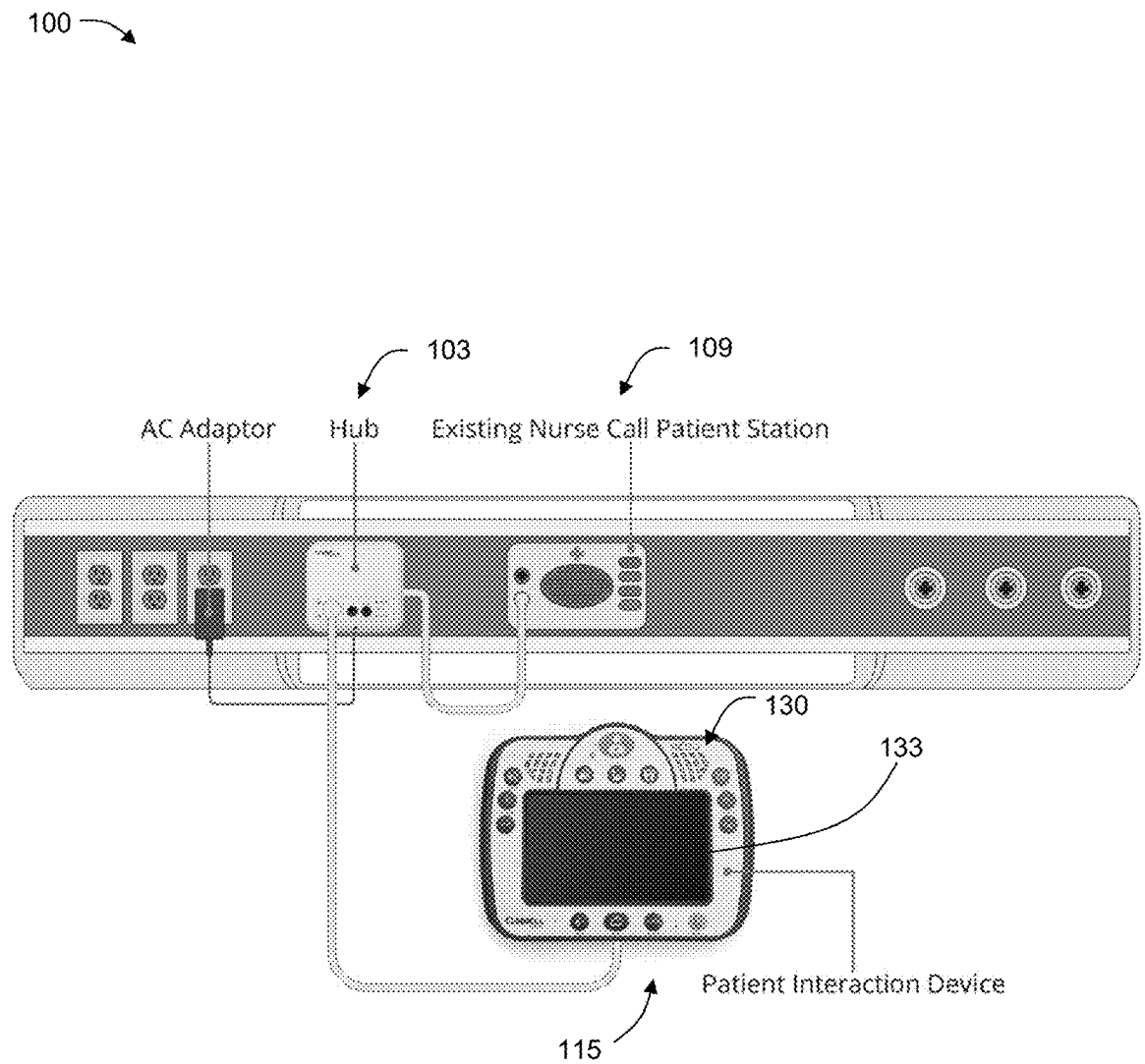
FIG. 2 is an embodiment of a nurse call system with a PID, patient hub, nurse call patient station.
Figure 3:
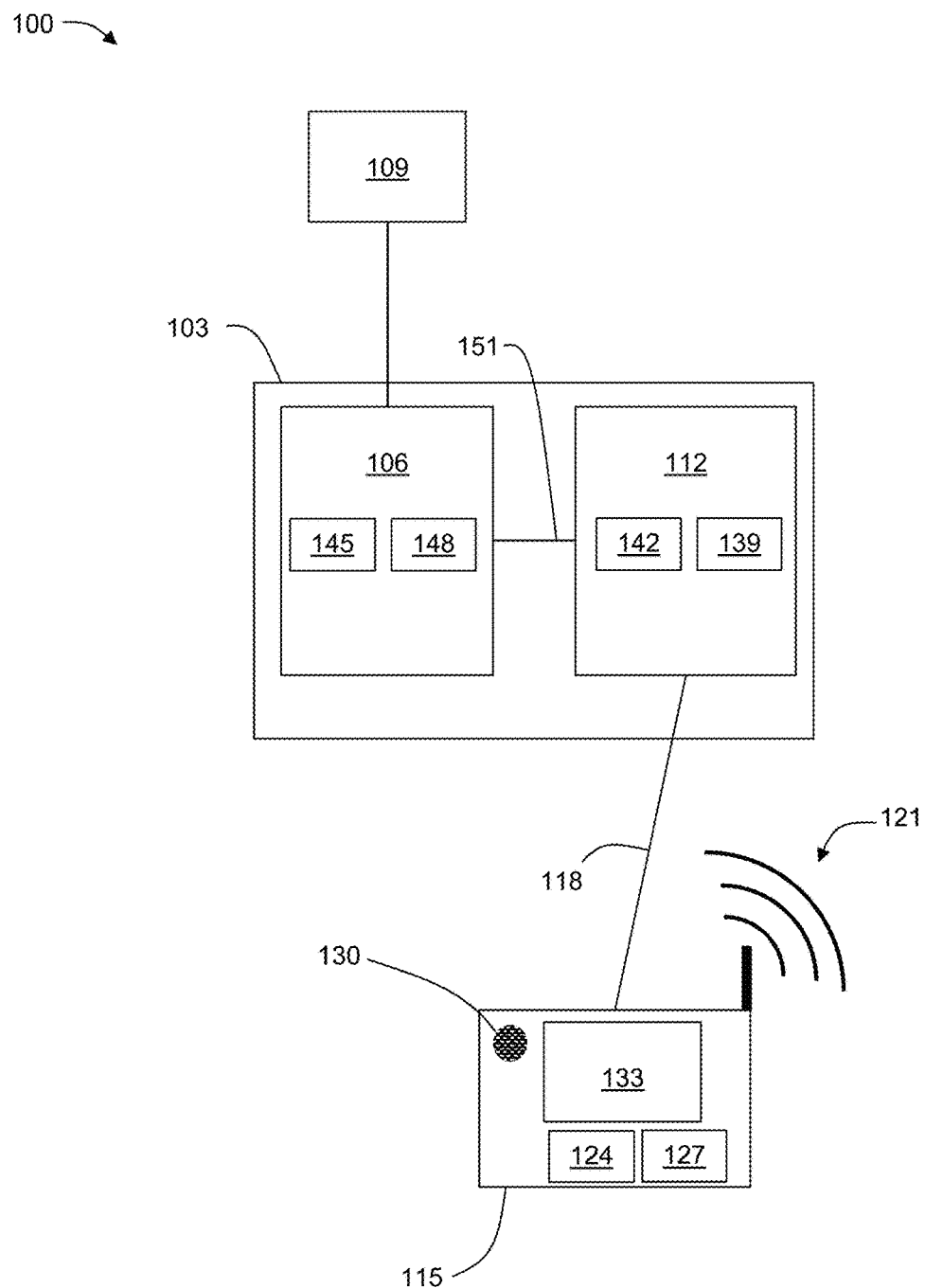
FIG. 3 is a schematic of an embodiment of the nurse call system as disclosed herein.

In an aspect of the present disclosure, a nurse call system 100 is presented. The nurse call system 100 may include a patient hub 103. The patient hub 103 may include a nurse call interface circuit 106 configured to be in electronic communication with a nurse call patient station 109. The patient hub 103 may further include a hub controller 112 in electronic communication with the nurse call interface circuit 106. The nurse call system 100 may further include a patient interaction device ("PID") 115. The PID 115 may be a pillow speaker. The PID 115 may include a hub interconnect 118 configured to be in electronic communication with the hub controller 112. The PID 115 may further include a wireless communication link 121 for receiving a PID software update. The PID software update may be a PID firmware update. The PID software update may be a PID operating system ("OS") update.

During manufacturing, a software client may be installed on the PID 115 for Mobile Device Management ("MDM") lifecycle maintenance via, for example, a cloud service. The software client may be any MDM software such as, for example AirWatch by VMware. The software client may be configured to securely connect to and synchronize with the MDM service through the Internet via, for example, the wireless communication link 121. The software client may be registered and/or authorized to download and install one or more software programs and/or updates provided by the MDM service. By synchronizing with the MDM service, the software client is able to determine the software programs, updates, configuration changes, and/or other modifications available to download to, install on, and/or apply to the PID 115.

The software program, updates, changes, etc. on the MDM service may be managed by, for example, the PID manufacturer by way of a remote console. For example, in the case of MDM provided as a cloud server, the PID manufacturer may access the service by logging into a web-based administrative interface over the Internet. From this interface, the manufacturer may upload software programs, updates, changes, etc., for distribution to all or a selected subset of devices. The MDM may also enable remote review and/or management of the software client of each PID 115 connected to the MDM service. Each PID 115 may be individually managed. Additionally or alternatively, a number of PIDs 115 may be managed as a group. For example, a set of PIDs 115 used for similar applications can be managed as a group. Software programs, updates, changes, etc., may be transmitted as a result of an affirmative action by the manufacturer, or they may be transmitted automatically from an external source, such as, for example, a build server. To update an OS of the PID 115, rather than a user-level application, a bootloader or similar program may be running on the PID 115 to allow for the OS update to be installed into a flash memory, a storage disk partition, etc., of the PID 115.

The PID 115 may further include a PID memory unit 124. The PID 115 may be configured to load a PID software update into the PID memory unit 124. In one embodiment, the PID 115 may be configured to load a PID software update into the PID memory unit 124 only if the PID software update has been verified as genuine. In an MDM embodiment in which the software programs and/or updates are for user-level applications, the MDM software client may be responsible for verification. The software client may be configured to connect with the MDM service in a secure fashion. The software client may first download the software programs and/or updates into memory or into a temporary disk partition or folder in a file system, and then subsequently verify the download (e.g., authenticate). In one example, this verification process may include checking a software checksum or cryptographic hash function to confirm all of the downloaded bits match the expected software checksum or hash.

In an embodiment in which software updates comprise updates to the OS or firmware of the PID 115, the use of public key cryptography may be used. In a particular example, the Rivest-Shamir-Adleman ("RSA") algorithm may be used, in which public/private key pairs are used to verify genuine software updates. An illustrative example of verification follows. First, a public key(s) is programmed into a processor of the PID 115 at a permanent, non-volatile, location such as an electronic fuse. An authorized software developer remotely creates a software "image" including the new software updates and the software image is cryptographically signed with a private key. The private key may be, for example, a one-way hash function calculated from the software image. Alternatively, the private key may be any other key generation algorithm as defined and supported by the RSA algorithm. The private key may perform RSA encryption as the signature. The private key is known only to the authorized software developer. To perform the update and authentication check, the PID may be configured to run bootloader software. This bootloader software may be configured to receive the remote software update, as well as temporarily storing it in memory or in a disk partition. The bootloader then uses the preprogrammed public key to verify the data bits of the software update as authentic, according to, for example, the RSA algorithm. The public key may perform RSA decryption as verification. The bootloader software may verify the software update either in real time as data packets are received, or after receiving the full update. Although an illustrative example using the RSA algorithm is provided, this example is non-limiting and other schemes may be used.

The PID 115 may further include a PID memory recovery module 127 configured to load a previous PID software version into the PID memory unit 124 if the PID software update fails to load. The PID software update may fail to load for a wide array of reasons. In one example, if the software update is transmitted by an MDM service over the Internet, the transmission may be interrupted by a lost Internet connection. The Internet connection may be lost for a variety of reasons, such as, for example, the MDM service becoming unavailable, Internet Service Provider ("ISP") issues with the Internet connection between the MDM service and the location of the PID 115, or congestion or failure of the hardware supporting the Internet connection, such as routers, switches, and modems. In another example, the wireless communication link 121 may be corrupted by an electronically noisy environment, prohibiting sufficient transmission data packets via the link. In another example, the wireless communication link 121 may be interrupted due to the placement of material with electromagnetic shielding properties around the PID 115. In another example, the bootloader software facilitating the OS or firmware update may become unresponsive, erratic, or even crash due to software bugs, unhandled exceptions or conditions, or other external events interfering with the software updating routine. In another example, hardware faults while transmitting data may cause a failure to load the PID software update.

The PID memory unit 124 may be divided into two or more partitions. For example, the PID memory unit 124 may be divided into a bootloader partition and an application partition. In a further example, the PID software update may only update one of the partitions, such as the application partition.

The PID 115 may be configured to produce a confirmation sound when the PID software update is successfully programmed into the PID memory unit 124. The confirmation sound may be produced by an audio speaker 130.

The PID 115 may be configured to produce a confirmation notice when the PID software update is successfully programmed into the PID memory unit 124. The confirmation notice may be shown by a display screen 133. In another embodiment, the one or more confirmation notices may be displayed while the software update is programming the PID memory unit 124. For example, the confirmation notices may display at stages or intervals of the PID software update installation, such as 25%, 50%, 75%, and 100% of completion.

The PID 115 may be further configured to receive a hub software update received via the wireless communication link 121. For example, the hub software update may be received in a similar manner to the PID software update described above. The PID 115 may be further configured to transmit the hub software update to the hub controller 112 via the hub interconnect 118. The PID 115 may be a pillow speaker. The hub software update may be a hub firmware update.

The hub controller 112 may include a hub memory unit 139. The hub controller 112 may be configured to load the hub software update into the hub memory unit 139. In one embodiment, the hub controller 112 may be configured to load the hub software update into the hub memory unit 139 only if the hub software update has been verified as genuine. The hub software update may be, for example, verified in a similar manner to the PID software update described above. The hub controller 112 may further include a hub memory recovery module 142 configured to load a previous hub software version into the hub memory unit 139 if the hub software update fails to load. The hub memory unit 139 may be divided into two or more partitions. For example, the hub memory unit 139 may be divided into a bootloader partition and an application partition. In a further example, the hub software update may only update one of the partitions, such as the application partition.

The PID 115 may be configured to produce a confirmation sound when the hub software update is successfully programmed into the hub memory unit 139. The confirmation sound may be produced by an audio speaker 130.

The PID 115 may be configured to display a confirmation notice when the hub software update is successfully programmed into the hub memory unit 139. The confirmation notice is shown by a display screen 133. In another embodiment, the one or more confirmation notices may be displayed while the software update is programming the hub memory unit 139. For example, the confirmation notices may appear at stages or intervals of the hub software update installation, such as 25%, 50%, 75%, and 100% of completion.

The PID 115 may be further configured to receive a nurse call software update received via the wireless communication link 121. The PID 115 may be further configured to transmit the nurse call software update to the hub controller 112 via the hub interconnect 118. The hub controller 112 may be configured to transmit the nurse call software update to the nurse call interface circuit 106 via an intrahub communication link 151. The nurse call software update may be a nurse call firmware update. The PID 115 may be a pillow speaker.

The nurse call software update procedure may utilize bootloader software residing on, for example, a nurse call interface circuit 106. This bootloader software is responsible for programming the nurse call software update into a proper memory location (such as, for example, flash memory) to allow for execution after reboot. The bootloader software may be an in-application programmer.

A primary difference between installing a nurse call software update, a hub software update, and a PID software update is the number of "hops" (or links) between devices within the nurse call system 100 required for each respective software update to reach its destination. As a PID software update is initially received by the PID 115 from the wireless communication link 121 and installed on the PID 115 itself, no "hops" are required. Regarding a hub controller software update, one "hop" is required to convey the update from the PID 115 to the hub controller 112. Regarding a nurse call software update, two "hops" are required to convey the update to the nurse call interface circuit 106; first, from the PID 115 to the hub controller 112 (hop one), and second, from the hub controller 112 to the nurse call interface circuit 106 (hop two).

As described above, the PID 115 may receive the update over the wireless communication link 121. The PID 115 may have a software application installed capable of recognizing a nurse call software update has been downloaded. In some embodiments, the PID 115 may be configured for triggering (remotely or locally) to begin a nurse call software update procedure. This software application may then issue a command across a communication channel to instruct the hub controller 112 to configure the nurse call interface circuit 106 into bootloader or in-application programmer mode. The communication channel may be a custom or any commonly-used communication channel. For example, the communication channel may be a Universal Serial Bus ("USB") or serial Universal Asynchronous Receiver-Transmitter ("UART") link. The command may be in the form of custom data packets. The PID 115 transmits the nurse call software update data to the hub controller 112, which the hub controller 112 then transmits to the bootloader of the nurse call interface circuit 106 for programming into memory. This transmission of data continues until the nurse call software update is fully programmed into memory. Once fully programmed, the PID 115, via the hub controller 112, may issue a reset command to the nurse call interface circuit 106. The reset command reboots the nurse call interface circuit 106 for the nurse call software update to load.

The nurse call interface circuit 106 may include a nurse call memory unit 145. The nurse call interface circuit 106 may be configured to load the nurse call software update into the nurse call memory unit 145. In one embodiment, the nurse call interface circuit 106 may be configured to load the nurse call software update into the nurse call memory unit 145 only if the nurse call software update has been verified as genuine.

Depending on the capabilities of the bootloader, the available hardware and/or software peripherals (such as support for public key cryptography), and the available size of program memory, the bootloader may verify the nurse call software update in a similar manner to the PID software update described above. The verification of the nurse call software update may occur upstream in the PID 115 or hub controller 112, as well as in the nurse call interface circuit 106. Based on the available program memory size and capabilities of their associated processors or microcontrollers, any of the three devices in the chain may store the public key used to verify the nurse call software update. The verification may occur either "on-the-fly" or after the entire update is received by the device and stored in an available memory location. In the case of the nurse call interface circuit 106 performing the verification, its memory may be allocated into "A" and "B" partitions. Both partitions may be large enough to store the nurse call software update, meaning the total memory space of the nurse call interface circuit is at least large enough to store two copies of the nurse call software update and the bootloader software. In one example, if the software update at memory location "A" is active (meaning it boots and runs when the nurse call interface circuit 106 is reset), then the software update is programmed to location "B". When the software update in location "B" is cryptographically verified, a non-volatile flag, such as a bit stored in Electrically Erasable Programmable Read-Only Memory ("EEPROM") or a flash memory location acting as an EEPROM, is set such that the bootloader knows to load the firmware at location B at next startup. Subsequently, location "A" is made available to receive the next software update.

The nurse call interface circuit 106 may further include a nurse call memory recovery module 148 configured to load a previous nurse call software version into the nurse call memory unit 145 if the nurse call software update fails to load.

The nurse call software update may fail to load for similar reasons as the PID software update described above, except that the nurse call update must travel through additional hardware communication paths and microcontrollers. These paths and microcontrollers may be corrupted by noise from electrostatic discharge ("ESD") events, power loss, physically broken connectors, wires, and/or traces, and bugs in the software update.

The nurse call memory unit 145 may be divided into two or more partitions. For example, the nurse call memory unit 145 may be divided into a bootloader partition and an application partition. In a further example, the nurse call software update may only update one of the partitions, such as the application partition.

The PID 115 may be configured to produce a confirmation sound when the nurse call software update is successfully programmed into the nurse call memory unit 106. The confirmation sound may be produced by an audio speaker 130.

The PID 115 may be configured to display a confirmation notice when the nurse call software update is successfully programmed into the nurse call memory unit 145. The confirmation notice may be shown by a display screen 133. In another embodiment, the one or more confirmation notices may be displayed while the software update is programming the nurse call memory unit 145. For example, the confirmation notices may appear at stages or intervals of the nurse call software update installation, such as 25%, 50%, 75%, and 100% completion.

Three examples of implementations of one or more of the embodiments of the disclosed nurse call system are provided below.

Example 1

Different varieties of advanced pillow speaker systems may comprise common hardware components to reduce the number of overall component part numbers (SKUs) required to manufacture the systems, and therefore reduce manufacturing cost by increasing the volume of production per SKU. However, it may be difficult, time consuming, error prone, costly, and/or entirely not possible to uniquely track each individual unit from production at the factory to installation in a particular room. Instead, it is highly desirable to implement a system to uniquely identify and register each unit at the factory. Once identified and registered, the unit may be installed in any room, and uniquely configured based on the care services offered in that particular room. At the factory, these units may be identified using a serial number and registered with software providing wireless, over-the-air (OTA) update capability. At the healthcare facility, the units may be identified in each room using their hardware MAC address when connected to an intranet. Similarly, the MAC address may be paired with the serial number stored on the device for pairing to the OTA software when securely connected to the Internet. At this point, the OTA software may install the desired software image designed for the room's care profile.

Example 2

In a second example, software updates are provided to pillow speaker systems that are already deployed when new features, improvements, and/or fixes to existing features are developed. In a traditional pillow speaker implementation, this is a long and costly process, wherein a patient room must first be unoccupied, and a technician must physically change or reconfigure the old unit. This process must be repeated room-by-room. Software updating is inflexible in this implementation, and compelling features may not be deployed simply because it is too difficult to update units. Using a wireless, OTA software update implementation, multiple rooms, entire wings or wards, or even larger groups of units may be automatically updated simultaneously as new or improved features are available. It may even be possible to update the unit without vacating the room if a hospital protocol to provide such an update determines the risk is acceptable. The reduced difficulty and cost of updating units makes updates more flexible, which in turn may drive greater adaptation of new and innovative patient care services.

Example 3

A third example involves patient turnover. Even in a case where a software image running on an advanced pillow speaker system is relatively static for the room or ward it occupies (making the services it provides similarly static), there may be patient registration, configuration, personal health, or other data stored in or at least processed by the unit. Wireless, OTA software updates may be used as a tool to "wipe" the unit by erasing the unit's memory and reinstall the software to restore it to default factory settings or baseline functional software in between sitting patients, thus ensuring confidentiality of data from patient to patient.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

We claim:

1. A nurse call system, comprising:
   a patient hub, comprising:
      a nurse call interface circuit configured to be in electronic communication with a nurse call patient station; and
      a hub controller in electronic communication with the nurse call interface circuit; and
   a patient interaction device ("PID"), comprising:
      a hub interconnect configured to be in electronic communication with the hub controller; and
      a wireless communication link for receiving a PID software update; and
   wherein the PID is further configured to receive a hub software update received via the wireless communication link, and to transmit the hub software update to the hub controller via the hub interconnect.

2. The nurse call system of claim 1, wherein the PID software update is a PID firmware update.

3. The nurse call system of claim 1, wherein the PID software update is a PID operating system update.

4. The nurse call system of claim 1, wherein the PID further comprises a PID memory unit, and the PID is configured to load the PID software update into the PID memory unit.

5. The nurse call system of claim 4, wherein the PID is configured to load the PID software update into the PID memory unit only if the PID software update has been verified as genuine.

6. The nurse call system of claim 4, wherein the PID further comprises a PID memory recovery module configured to load a previous PID software version into the PID memory unit if the PID software update fails to load.

7. The nurse call system of claim 4, wherein the PID is configured to produce a confirmation sound when the PID software update is successfully programmed into the PID memory unit.

8. The nurse call system of claim 7, wherein the confirmation sound is produced by an audio speaker.

9. The nurse call system of claim 4, wherein the PID is configured to produce a confirmation notice when the PID software update is successfully programmed into the PID memory unit.

10. The nurse call system of claim 9, wherein the confirmation notice is shown by a display screen.

11. The nurse call system of claim 1, wherein the PID is a pillow speaker.

12. The nurse call system of claim 1, wherein the hub software update is a hub firmware update.

13. The nurse call system of claim 1, wherein the hub controller comprises a hub memory unit, and the hub controller is configured to load the hub software update into the hub memory unit.

14. The nurse call system of claim 13, wherein the hub controller is configured to load the hub software update into the hub memory unit only if the hub software update has been verified as genuine.

15. The nurse call system of claim 13, wherein the hub controller further comprises a hub memory recovery module configured to load a previous hub software version into the hub memory unit if the hub software update fails to load.

16. The nurse call system of claim 13, wherein the PID is configured to produce a confirmation sound when the hub software update is successfully programmed into the hub memory unit.

17. The nurse call system of claim 16, wherein the confirmation sound is produced by an audio speaker.

18. The nurse call system of claim 13, wherein the PID is configured to display a confirmation notice when the hub software update is successfully programmed into the hub memory unit.

19. The nurse call system of claim 18, wherein the confirmation notice is shown by a display screen.

20. The nurse call system of claim 1, wherein the PID is a pillow speaker.

21. The nurse call system of claim 1, wherein the PID is further configured to receive a nurse call software update received via the wireless communication link and to transmit the nurse call software update to the hub controller via the hub interconnect, and wherein the hub controller is configured to transmit the nurse call software update to the nurse call interface circuit via an intrahub communication link.

22. The nurse call system of claim 21, wherein the nurse call software update is a nurse call firmware update.

23. The nurse call system of claim 21, wherein the nurse call interface circuit comprises a nurse call memory unit, and the nurse call interface circuit is configured to load the nurse call software update into the nurse call memory unit.

24. The nurse call system of claim 23, wherein the nurse call interface circuit is configured to load the nurse call software update into the nurse call memory unit only if the nurse call software update has been verified as genuine.

25. The nurse call system of claim 23, wherein the nurse call interface circuit further comprises a nurse call memory recovery module configured to load a previous nurse call software version into the nurse call memory unit if the nurse call software update fails to load.

26. The nurse call system of claim 23 wherein the PID is configured to produce a confirmation sound when the nurse call software update is successfully programmed into the nurse call memory unit.

27. The nurse call system of claim 26, wherein the confirmation sound is produced by an audio speaker.

28. The nurse call system of claim 23, wherein the PID is configured to display a confirmation notice the nurse call software updated is successfully programmed into the nurse call memory unit.

29. The nurse call system of claim 28, wherein the confirmation notice is shown by a display screen.

30. A nurse call system, comprising:
a patient hub, comprising:
- a nurse call interface circuit configured to be in electronic communication with a nurse call patient station; and
- a hub controller in electronic communication with the nurse call interface circuit; and a patient interaction device ("PID"), comprising:
- a hub interconnect configured to be in electronic communication with the hub controller; and
- a wireless communication link for receiving a PID software update; and wherein the PID is further configured to receive a nurse call software update received via the wireless communication link and to transmit the nurse call software update to the hub controller via the hub interconnect, and wherein the hub controller is configured to transmit the nurse call software update to the nurse call interface circuit via an intrahub communication link.

* * * * *